(12) United States Patent
Massoud

(10) Patent No.: US 8,262,665 B2
(45) Date of Patent: Sep. 11, 2012

(54) SURGICAL GUIDE FOR USE DURING SINUS ELEVATION SURGERY UTILIZING THE CALDWELL-LUC OSTEOTOMY

(76) Inventor: Yehia A. Massoud, New York, NY (US)

( * ) Notice: Subject to any disclaimer, the term of this patent is extended or adjusted under 35 U.S.C. 154(b) by 162 days.

(21) Appl. No.: 12/592,392

(22) Filed: Nov. 23, 2009

(65) Prior Publication Data

US 2010/0191242 A1    Jul. 29, 2010

Related U.S. Application Data

(63) Continuation-in-part of application No. 10/810,553, filed on Mar. 29, 2004, now Pat. No. 7,621,744.

(51) Int. Cl.
*A61C 5/00* (2006.01)
(52) U.S. Cl. .......... 606/96; 128/898; 623/17.17
(58) Field of Classification Search .......... 433/72, 433/75–76, 215; 128/898; 623/17.17; 606/87, 606/96, 86 R
See application file for complete search history.

(56) References Cited

U.S. PATENT DOCUMENTS

| | | | |
|---|---|---|---|
| 4,971,557 A | 11/1990 | Martin | |
| 5,320,529 A | 6/1994 | Pompa | |
| 5,397,235 A | 3/1995 | Elia | |
| 5,558,622 A | 9/1996 | Greenberg | |
| 5,711,315 A | 1/1998 | Jerusalmy | |
| 5,746,743 A | 5/1998 | Greenberg | |
| 5,927,982 A | 7/1999 | Kruger | |
| 5,989,025 A | 11/1999 | Conley | |
| 6,235,035 B1 | 5/2001 | Boukhris | |
| 6,391,016 B2* | 5/2002 | Bays | 604/506 |
| 7,125,253 B2* | 10/2006 | Kitamura et al. | 433/173 |
| 7,621,744 B2 | 11/2009 | Massoud | |
| 2005/0021142 A1 | 1/2005 | Ganz | |
| 2006/0287732 A1 | 12/2006 | Pezeshkian | |
| 2008/0182225 A1 | 7/2008 | Gordils Wallis | |

* cited by examiner

*Primary Examiner* — Cris L Rodriguez
*Assistant Examiner* — Hao D Mai
(74) *Attorney, Agent, or Firm* — Abelman, Frayne & Schwab

(57) ABSTRACT

The present invention discloses a surgical guide and accompanying depth bur with a method for its use during sinus elevation surgery utilizing the Caldwell-Luc Osteotomy procedure. The surgical guide of the present invention provides accurate transfer of the parameters of the surgical osteotomy to be performed during sinus elevation surgery. It bridges the gap between the precise information obtained from the CT scan and the surgical field on which this surgical plan must be placed. This is accomplished by the use of the surgical guide which is constructed based on the information in the CT scan and the treatment plan prepared utilizing 3-D imaging software.

20 Claims, 12 Drawing Sheets

SURGICAL GUIDE FOR USE DURING SINUS ELEVATION SURGERY UTILIZING THE CALDWELL-LUC OSTEOTOMY

CROSS REFERENCE TO RELATED APPLICATION

This patent application is a Continuation-in-Part of U.S. patent application Ser. No. 10/810,553, filed Mar. 29, 2004 now U.S. Pat. No. 7,621,744, the contents of which are incorporated herein by reference in its entirety.

FIELD OF THE INVENTION

The present invention relates generally to the field of oral implantology in the surgical reconstruction of the maxillary sinus in preparation for dental implant placement. More particularly, the present invention relates to a surgical guide and accompanying bur utilized to guide the surgeon in preparation of the osteotomy to enter the maxillary sinus as part of the procedure of sinus elevation and grafting.

BACKGROUND OF THE INVENTION

Following maxillary posterior tooth loss, the maxillary sinus pneumatisizes or expands in every dimension towards the maxilla. As the maxillary bone resorbs, the sinus is enlarged in a coronal, lateral, anterior and posterior direction. This pneumatization, or expansion of the maxillary sinus resulting from maxillary bone resorption, leaves less maxillary bone for a platform on which to place dental implants. If enough maxillary bone has resorbed, placement of a dental implant would penetrate the floor of the sinus and leave the apical portion of the implant exposed in the sinus and, thus, not engaged in bone. This would result in no bony support around that portion of the implant and negate the purpose for dental implant placement as a means of tooth replacement in the posterior maxilla.

In preparation for dental implant placement in the posterior maxilla, the clinician must evaluate the position of the maxillary sinus relative to the remaining maxillary bone and whether bone resorption has occurred to the point of leaving insufficient amounts of bone for implant placement. If it is determined that insufficient bone exists for placement of dental implants due to the expansion of the maxillary sinus, then a sinus elevation and grafting procedure is indicated prior to implant placement.

The prevalent method of sinus elevation and grafting is called the Caldwell-Luc Osteotomy. The procedure involves reflecting a full thickness mucosal flap to expose the lateral wall of the sinus and maxilla. A lateral osteotomy is then prepared in the lateral wall of the maxillary sinus. The osteotomy is rectangular in shape and is cut as deep as the lateral wall of the maxillary sinus until the sinus membrane (Schneiderian membrane) is exposed. The window, or osteotomy, is then carefully tapped medially to allow entry into the sinus cavity. Afterwards, the sinus membrane is gently elevated from the floor and the anterior and posterior walls of the sinus utilizing various blunt dissecting instruments. After the sinus membrane has been elevated and retracted apically and medially, bone is then placed in the area that the sinus membrane has been elevated from. The mucosal flaps are then approximated and sutured.

One of the technical difficulties encountered during this procedure is the inability of the operator to precisely locate the floor of the sinus as he prepares the osteotomy from an antero-posterior direction (along the X-Y axis). Since the floor of the sinus can elevate and descend variably as the osteotomy moves antero-posteriorly, it is impossible to visualize this course. Therefore, the osteotomy is generally prepared in a straight line higher than the highest point of the sinus floor. This guarantees penetration into the sinus floor since an osteotomy that is lower than the sinus floor at any point will simply penetrate into the maxillary bone and not into the sinus cavity. This would require adjustment by expanding the osteotomy superiorly (apically) in order to penetrate the sinus cavity. Obviously, the additional trimming of bone is traumatic and removes bone unnecessarily.

Another error occurs if the osteotomy is placed too superior to the floor of the sinus. Very careful manipulation must then be effected in order to negotiate the remaining lateral wall of the sinus inferior to the osteotomy and to descend below the Schneiderian membrane in order to elevate it from the sinus floor. This technically difficult maneuvering of the instruments along two planes increases the risk of tearing the membrane and thus compromising the outcome of the graft. Otherwise, the osteotomy must be adjusted by expanding in an inferior direction. This would lead to additional trimming of bone and increase the risk of tearing the membrane during the expansion of the osteotomy. It is nearly impossible to visualize the variable course of the sinus floor as the osteotomy progresses antero-posteriorly. This inability to visualize the course of the sinus floor is the first difficulty encountered in the procedure.

Another difficulty encountered is the varying thickness of the lateral wall of the sinus as the osteotomy penetrates it to expose the underlying Schneiderian membrane. The operator must penetrate fully through the lateral wall (X-Z axis) in order to raise the window and elevate the membrane. However, if the osteotomy is prepared too deep, it can tear through the fragile membrane. Therefore, great operator skill is required to visualize the membrane as the osteotomy is prepared through a varying depth of the lateral wall and the membrane is approached.

A further difficulty encountered is the anterior wall of the sinus. Besides the varying depth of the lateral wall, the anterior wall can also vary in course in the Y-X axis (FIG. 2) just as the floor can vary in course in the X-Y axis (FIG. 2) and the lateral wall can vary in thickness in the Y-Z axis (FIG. 3). Since the osteotomy usually is placed in a straight line apicocoronally (vertically), whereas the anterior wall is usually not a straight line, portions of the osteotomy would be too far posterior to the anterior wall. This would require manipulation anteriorly and then laterally to dissect the membrane from the lateral and anterior walls thus increasing the risk of tearing the membrane from the difficult manipulation in two planes. Again, any additional adjustments to the osteotomy would cause unnecessary bone removal and trauma as well as increase the risk of tearing the membrane.

Most of this technique relies on the careful approximation of the outline of the area of the sinus to be grafted. The osteotomy planned should be inside the sinus borders for reasons explained above. Since it is nearly impossible to accurately follow the varying course of the sinus during the osteotomy, inevitably there would be areas that are not exposed by the osteotomy. This would require the careful manipulation of the sinus membrane which risks damage to the membrane. Furthermore, as the lateral wall of the sinus is being cut, the varying thickness of the lateral wall requires that the surgeon proceed very carefully and rely on visual as well as tactile senses to establish that the wall has been pierced without entering the sinus so as to not damage the immediately underlying membrane.

One of the most reliable methods to graph the maxillary sinus in three dimensions is through a computerized axial tomography (CAT or CT) scan that renders the sinus in the X, Y and Z planes. The CT scan can then be formatted for evaluation utilizing three-dimensional (3-D) imaging software. The 3-D imaging software allows the clinician to view the sinus in all dimensions as well as to manipulate the image and prepare a treatment plan as to the location and amount of bone to be grafted in the sinus in order to augment the missing maxillary bone that the sinus has expanded into. This information can then be utilized by the surgeon to establish the parameters of outline and volume of the area of the sinus to be entered for bone grafting.

Even with the information provided by the CT scan utilizing the 3-D imaging software as to the outline of the sinus in the X, Y and Z planes and all other parameters, there has been no mechanism to accurately transfer this highly precise information to the surgical field. Meticulous planning of the parameters of the sinus to be elevated and augmented has been thwarted by the inaccurate approximation in the transfer of this information during the surgical procedure.

There has thus been a gap between the extremely precise diagnostic information and treatment planning obtained by the CT scan and 3-D imaging software, and the accurate transfer of that information into the surgical field to aid the surgeon in executing such a treatment plan.

Accordingly, the objects of the device and method of the present invention are to overcome the limitations and drawbacks of the prior art and provide a significant contribution to the state of the art of reconstructive surgery of the maxillary sinus by providing a surgical guide and bur and a specific method of use wherein the guide has the advantages associated with transferring precise data obtained from a CT scan utilizing 3-D imaging software into the surgical field and aiding the surgeon in such surgery.

SUMMARY OF THE INVENTION

The invention described discloses a surgical guide and accompanying surgical bur with a ledge for depth control. The guide is fabricated from acrylic and is based on the treatment plan set forth from the diagnostic information provided by 3-D imaging software from a CT scan taken of a patient. The surgical guide is shaped and dimensioned (i.e., customized) based on the CT scan and 3-D imaging software results of the sinus area for each patient and accordingly, allows the surgeon to accurately prepare a Caldwell-Luc osteotomy in all three planes. The outline of the osteotomy, as well as the depth of the bone to be removed without damaging the underlying the Schneiderian Membrane is created utilizing the surgical guide and proper depth bur. This permits open access to the maxillary sinus cavity within the dimensions required for the sinus elevation and enables the surgeon easy access to the Schneiderian Membrane without anatomical obstructions.

Previously, this procedure was performed merely with an approximation as to where the floor of the sinus was, where the superior portion was, as well as where the anterior wall and the posterior wall are located. In addition, the variable depth of the lateral wall of the sinus was accessed only with the experience and visual sense of the clinician without exact measurements as to the varying thickness of the osteotomy as it moved along the x-y axis. The surgical guide of the present invention eliminates all approximations of the osteotomy in the x-y axis as to the outline of the osteotomy, as well as along the Z axis as to the depth of the osteotomy so as to prevent any damage of overcutting into the Schneiderian Membrane, and thus enabling easy access into the sinus cavity as outlined by the treatment plan set forth utilizing 3-D imaging software from a CT scan of the patient's maxillary sinus.

BRIEF DESCRIPTION OF THE DRAWINGS

FIGS. 9 and 10 collectively depict an embodiment of a custom configured, multi-sectional surgical guide suitable for performing the osteotomy, in which FIG. 9 illustrates a top perspective view of a first portion, and FIG. 10 illustrates a top perspective view of a second portion of the multi-section surgical guide.

To facilitate understanding of the invention, identical reference designations have been used, when appropriate, to designate the same or similar elements that are common to the figures. Further, unless stated otherwise, the drawings shown and discussed in the figures are not drawn to scale, but are shown for illustrative purposes only.

DETAILED DESCRIPTION OF THE INVENTION

Figure 1:
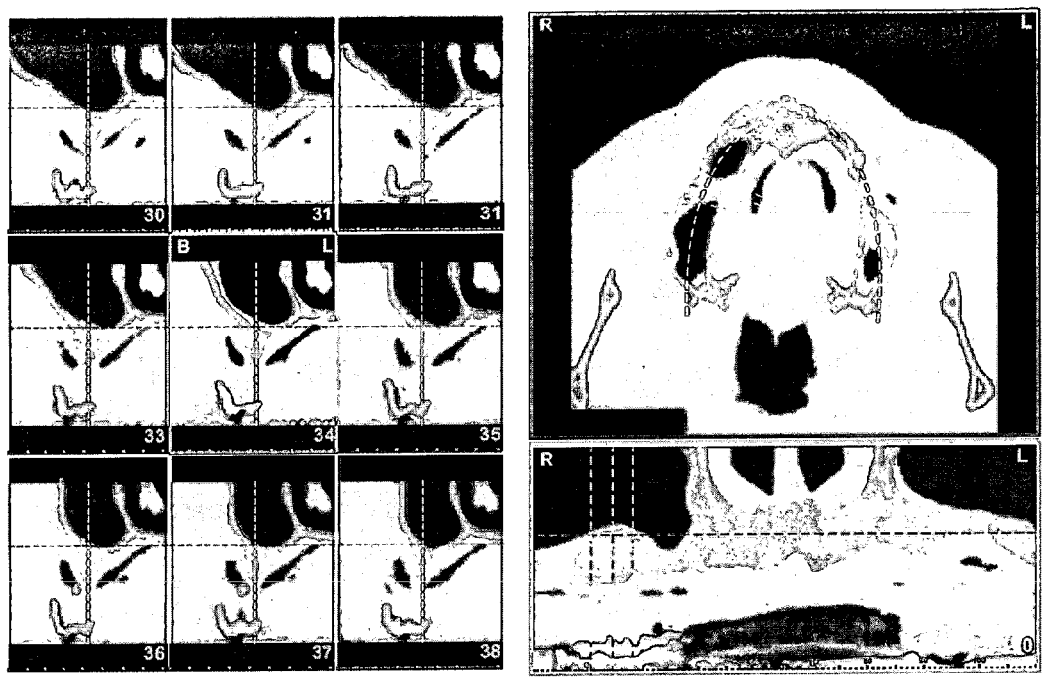
FIG. 1 is an image from a CT scan showing three views.
Figure 2A:
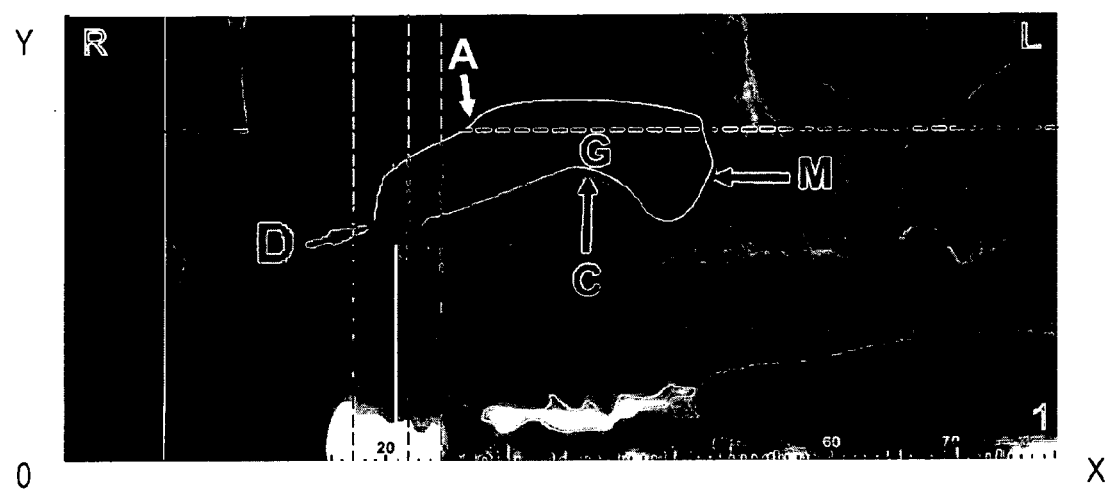
FIG. 2A is the same panoramic view as FIG. 2 showing the design of the area to be grafted G along the X-Y axis.
Figure 3:
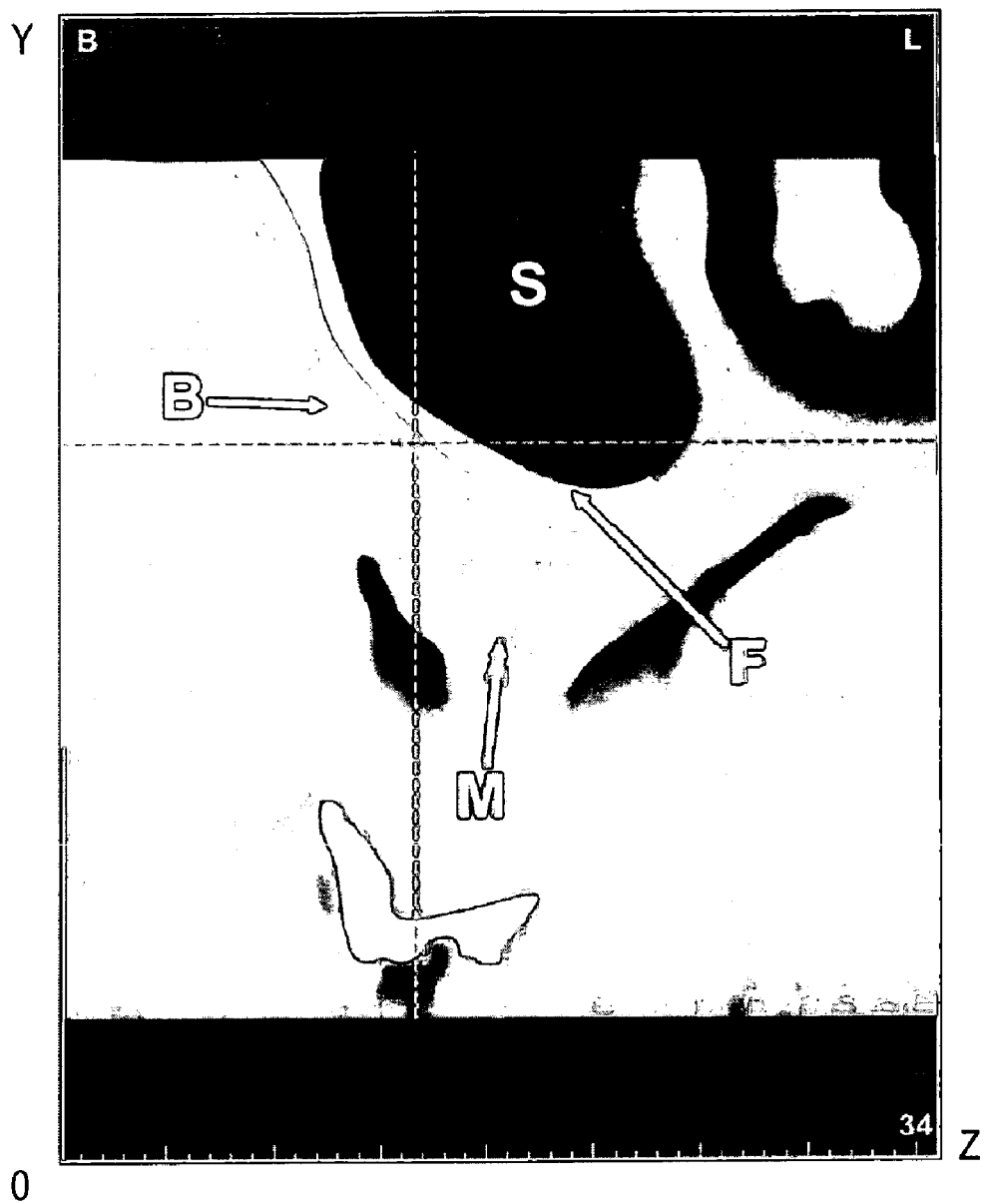
FIG. 3 shows cross sectional views of the maxilla and sinus at 1 mm intervals.
Figure 3A:
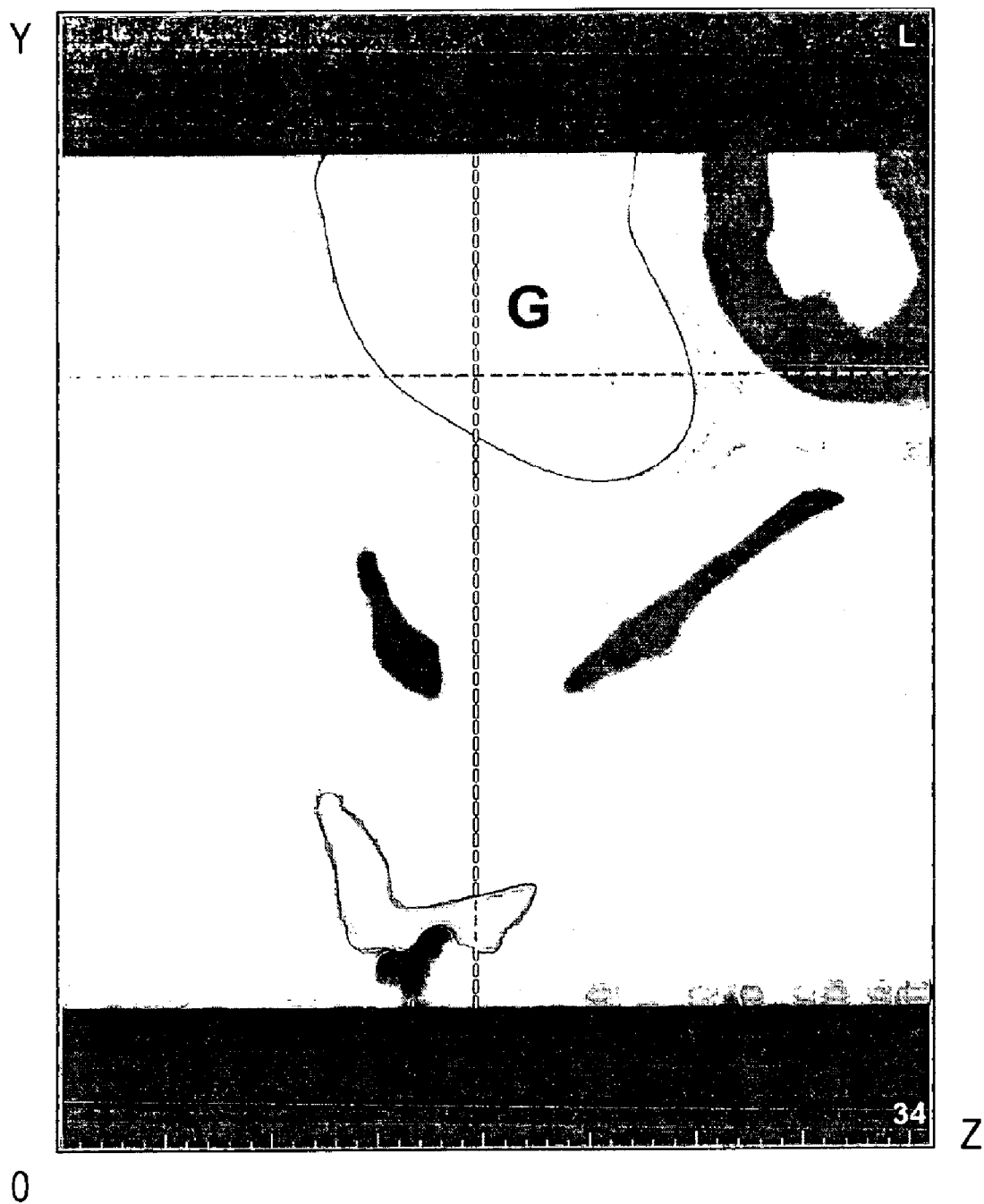
FIG. 3A is the same cross section as FIG. 3 showing the design of the area to be grafted G as well as the Y-Z axis.

In the oral cavity, when there is tooth loss, the maxillary sinus pneumatisizes, meaning that there is resorption in a three dimensional plane. The floor of the sinus drops towards the oral cavity, as well as resulting in expansion of the lateral walls. This leaves less maxillary bone for placement of an implant to replace the missing teeth. If the remaining maxillary bone is insufficient to support an implant in terms of height and width, then sinus elevation and bone grafting is required in order to regain the resorbed bone. The treatment planning for the sinus elevation involves the patient to receive a CT scan which provides different views of the sinus and maxillary bone (FIG. 1). This diagnostic information allows the surgeon to prepare a treatment plan which outlines the volume and borders of the area of the sinus to be grafted (FIGS. 2A and 3A).

Referring to FIG. 1, nine sagittal cross-sectional CT scan views along the Y-Z axes are illustratively shown for a patient under treatment on the left side of the drawing. Each of the nine cross-sectional views represents a slice at a particular millimeter (mm) marking (i.e., 30 mm through 38 mm). The CT scan view located on the upper right portion of FIG. 1 is an axial CT scan through the maxillary antrum, and the CT scan view located on the lower right portion of FIG. 1 is a panoramic view along the X-Y axes.

Figure 2:
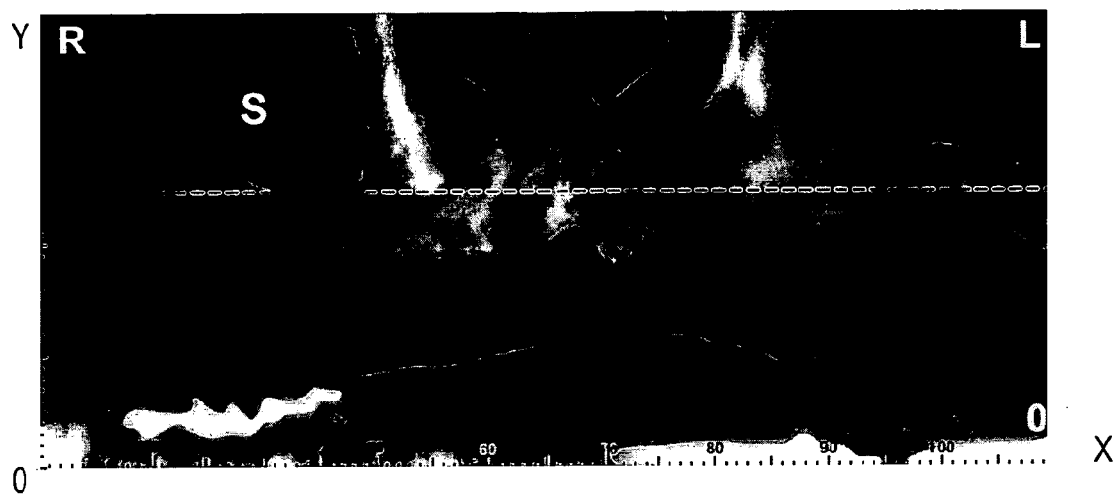
FIG. 2 shows a panoramic view of the maxilla showing the right and left sinuses (S) along the X-Y axes.

Referring to FIG. 2, an enlarged panoramic view of the CT scan of the lower right portion of FIG. 1 is illustratively shown. The panoramic view is along the X-Y axes, where the right side of the patients face is labeled "R" and the left side of the patients face is labeled "L". The X-Y axes are scaled in millimeters. For example, the X-axis includes one millimeter interval markings starting from twenty (20) mm on the right side of the patient's upper jaw and continuing left to one hundred and ten (110) mm.

The panoramic view of the patient's upper jaw (maxilla) and sinuses illustratively includes a horizontal broken line extending across the CT scan that represents a sinus membrane floor positioning line. The sinus membrane floor positioning line illustrates that the right sinus (darkened portion labeled "S") has two sinus portions that extend below sinus floor membrane and a central portion that extends above sinus floor membrane. Accordingly, FIG. 2 illustrates that the sinus floor is uneven along the X-axis which may have been caused by resorbtion of the coronal portion of the maxillary bone.

FIG. 2A is an exploded view of the right sinus area of the panoramic view of FIG. 2. FIG. 2 further illustrates the design of the area to be grafted "G" along the X-Y axis. Reference designation (A) is the apical portion of the area to be grafted; (C) is the coronal portion; (M) is the mesial or anterior portion; and (D) is the distal or posterior portion of the area of the sinus to be grafted.

Referring to FIG. 1, as noted above, the right portion of the drawing illustrates nine (9) cross-sectional views (Z-Y slices) as taken at the 30, 31, 32, 33, 34, 35, 36, 37, and 38 mm points along the X-Y axes (FIG. 2). FIG. 3 is an enlarged cross sectional sagittal view of the maxilla and sinus at the 34 mm point (FIG. 1) along the X-axis of the panoramic view of the maxilla of FIG. 2.

Referring now to FIG. 3, the Z-Y axes are also measured and marked in one millimeter intervals. The arrow (B) indicates the buccal or lateral wall of the sinus, the arrow (F) indicates the floor of the sinus, and the arrow (M) indicates the maxilla (upper jaw) bone. The darkened area labeled (S) is the sinus area above the maxilla jaw bone. The sinus area (S) includes areas (darkened portion) that extend below the broken horizontal sinus membrane floor positioning line, as well as areas that extend beyond the desired depth towards the lateral wall of the sinus (S) along the Z-axis, as illustrated by the depth positioning line drawn as the broken line extending vertically along the Y-axis.

FIG. 3A is the same view as FIG. 3 along the Y-Z axes. FIG. 3A illustrates the portion of the maxilla receiving the bone graph (G).

Figure 3B:
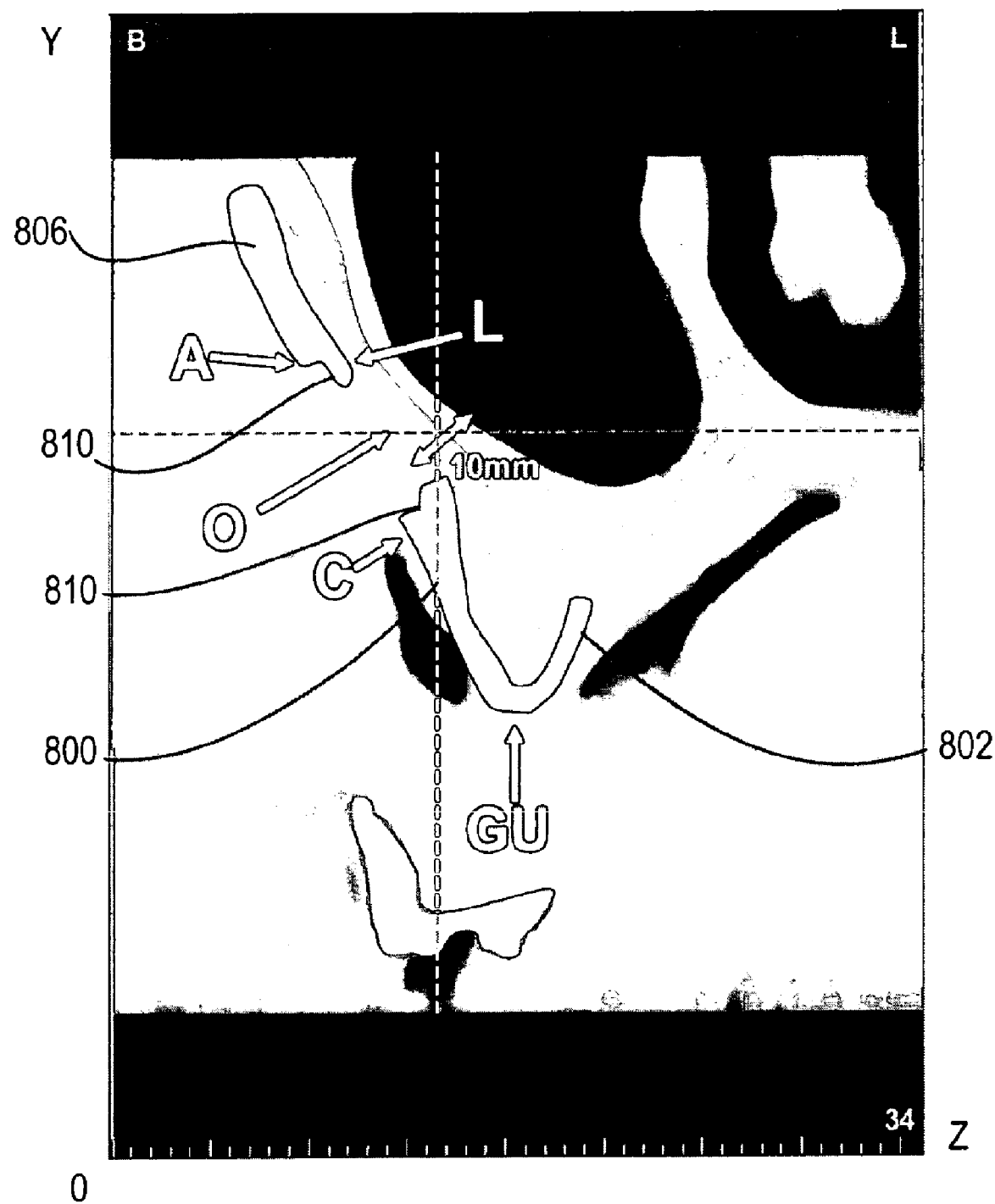
FIG. 3B is the same cross section as FIG. 3 with a surgical guide in position in accordance with the present invention.

FIG. 3B is also the same cross sectional view as shown in FIG. 3 and includes the customized surgical guide (GU and 800 of FIG. 8) of the present invention placed in position along the maxilla to enable the osteotomy in accordance with the present invention and prior to performing the bone graph. The apical (arrow A) and coronal (arrow C) borders of the osteotomy are formed within the guide. As discussed below in greater detail, the ledge (L) of the guide maintains the standard thickness of 10 mm to penetrate the buccal wall (B) of the sinus (S).

One method which is prevalent for providing sinus elevation and bone grafting is the Caldwell-Luc Osteotomy. This procedure involves providing an opening or window in the lateral wall of the sinus (reference "O" in FIG. 7), and then elevating the sinus membrane (Schneiderian Membrane) in order to place a bone graft to replace the resorbed bone in the floor and lateral wall of the sinus.

Figure 6:
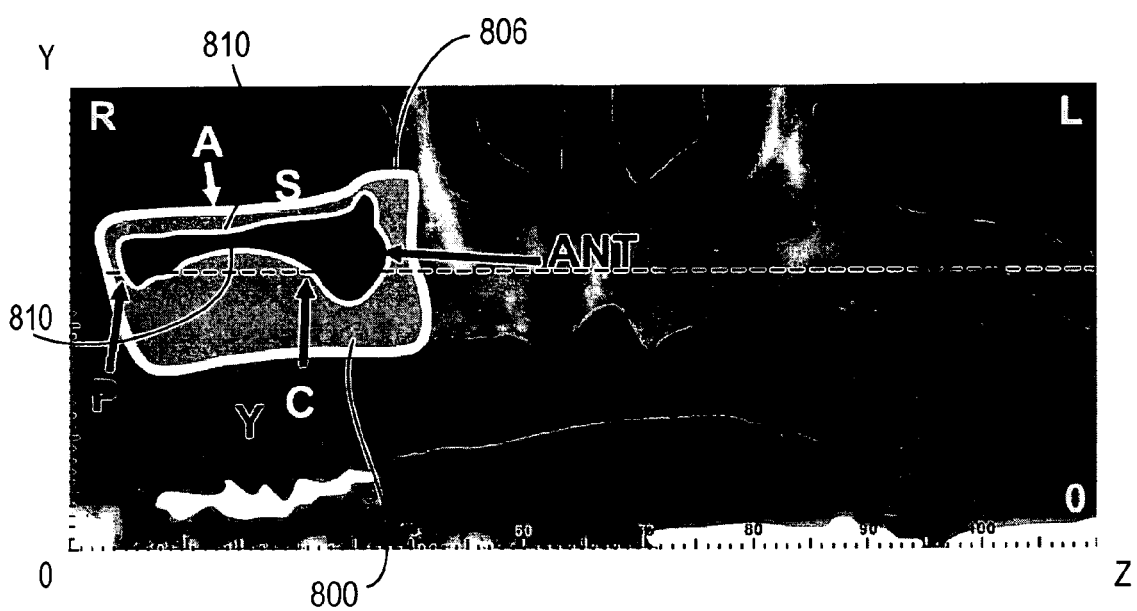
FIG. 6 is a panoramic view of the surgical guide G in position showing the outline of the osteotomy with the coronal C, apical A, anterior ANT, and posterior P aspect of the osteotomy.

The outline of the osteotomy is dictated by the area that is required to be grafted. Since it is a three dimensional osteotomy, there is an X, Y and Z component in the plane of the osteotomy. The X and Y component outlines the apical, coronal, mesial and distal aspect of the osteotomy (FIG. 6). The Z component outlines the depth of the osteotomy as dictated by the thickness of the lateral wall of the sinus (FIG. 3). As a surgeon prepares the osteotomy, he approximates the height of the floor of the sinus as it varies as he travels anteroposteriorly (FIG. 2).

Furthermore, the surgeon approximates the mesial (anterior) extent in a coronal-apical direction as well as the distal (posterior) extent in a coronal-apical direction. The surgeon also approximates the occlusal outline of the osteotomy as it connects the mesial and distal (anterior and posterior) walls of the osteotomy (FIG. 6). More importantly, the surgeon must then determine the depth laterally, along the Z axis, of the osteotomy within his outline (FIG. 3) so as to penetrate up to the Schneiderian Membrane. This lateral depth varies as the surgeon moves along the X-Y plane along the outline form. The methodology traditionally available is the surgeon's view of the color of the bone as it changes as he approaches the piercing of the lateral wall and sees the grayish colored Schneiderian Membrane.

After the surgeon has cut the outline form of the osteotomy and penetrated the lateral wall of the sinus (FIG. 7), the surgeon begins to elevate the membrane from the floor of the sinus and graft bone in the site. Rarely, does the surgeon place his osteotomy exactly on the floor of the sinus (the coronal border) and along the exact anterior border of the sinus. Therefore, the surgeon must maneuver the instruments as to separate the membrane from the sinus floor and anterior and posterior walls as there is inevitably a shelf of bone to negotiate.

To assist the surgeon in visualizing the outline of the sinus in three dimensions, a patient can have a CT scan (e.g., DENTASCAN®) performed and formatted by a 3-D imaging computer program (e.g., SIMPLANT®) which gives different views of the X, Y and Z planes of the sinus (see, e.g., FIG. 1). This allows the surgeon to visualize the different walls of the sinus and identify their exact depths and outline for the osteotomy. Furthermore, the exact outline in the X-Y axis (antero-posteriorly) can be drawn and planned so the osteotomy is exactly at the floor of the sinus regardless of variations in height as the osteotomy travels along the X axis (FIG. 6). In addition, the anterior and posterior walls of the osteotomy can be charted so they follow along the exact walls of the sinus, thus leaving no shelves for the sinus elevation instruments to negotiate. The superior wall is also outlined as necessary by the height of bone required to be grafted.

Finally, and no less important, as the osteotomy moves along the X-Y plane in preparing the window, the depth of the osteotomy, as dictated by the thickness of the lateral wall (the Z axis) (see FIG. 3b), can also be accurately measured as it varies along the X-Y plane. All this information can be planned as well as visualized by the surgeon, prior to surgery, utilizing the 3-D imaging software. However, to date, there has been no available mechanism to transfer this information into a reliable guide for the surgeon to follow the parameters he/she has outlined in the treatment plan.

In one aspect of the present invention, a customized surgical guide (800 shown in FIG. 8) is fabricated from acrylic which will replicate the parameters outlined by the surgeon according to the plan proposed utilizing the 3-D imaging software obtained from a CT scan. These parameters will assist in preparation of a Caldwell-Luc osteotomy that is appropriate to the particular, unique and irregular shape of the maxillary bone established by the treatment plan set forth by the surgeon in the X-Y and Z axes, thereby transferring the information from the computer to a guide that can be utilized during the surgical procedure. The guide is to be seated on the alveolar ridge after dissection of the mucosa. The seat is a firm, stable seat without any movement. In one embodiment an orifice is provided through the guide wall to enable a fastener, such as a screw to be inserted through and into the maxilla bone to securely retain the guide in place.

Figure 8:
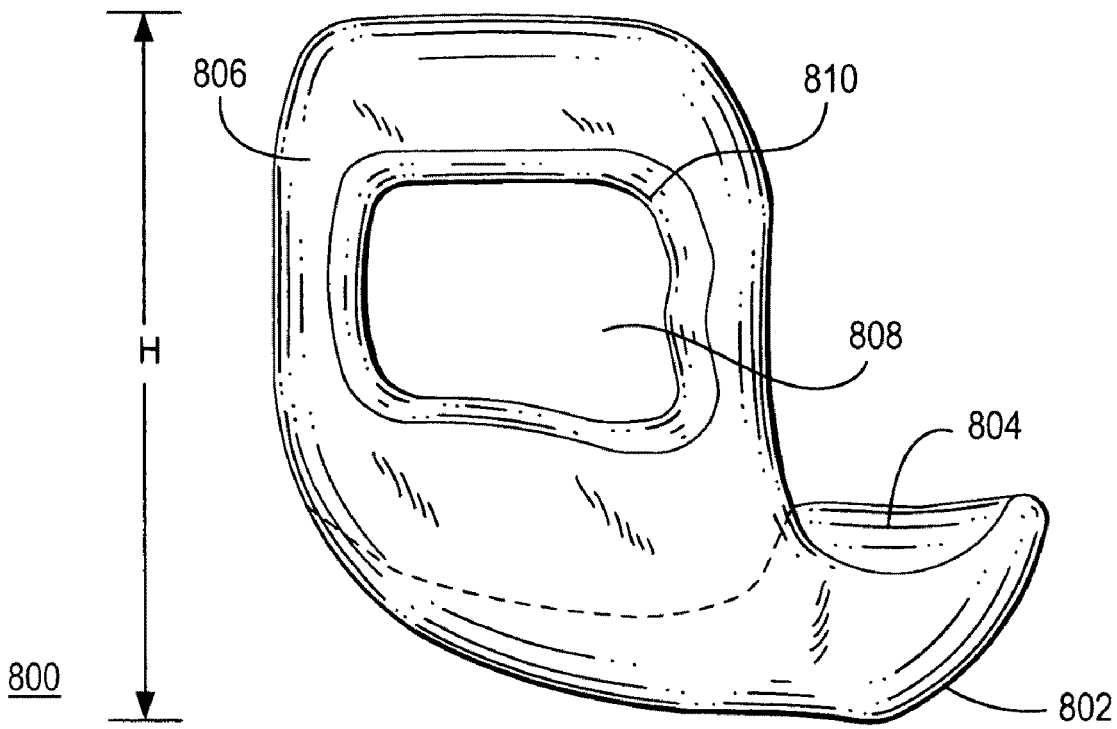
FIG. 8 is a top perspective view of the surgical guide illustrating a window corresponding with the outline of the osteotomy to be prepared with the apical wall (A), inferior or coronal wall (C), anterior wall (ANT), and posterior wall (P) of the sinus.

Referring now to FIG. 8, the customized surgical guide 800 is curvi-linear in shape and is sized and shaped to correspond to the upper jaw (maxilla) and sinus shape of a particular patient, as determined by the CT scan and 3-D imaging software previously administered to the patient. As illustratively shown in the drawing, the surgical guide 800 includes a curved lower portion 802 having an upper surface 804 adapted for positioning along the lower edge of the maxilla (alveolar ridge) or the upper teeth (e.g., molars). The curved lower portion extends in an upward direction to form a second portion 806 having an overall height "H" an, overall width "W", and an overall thickness or depth "D".

The upward extending second portion 806 includes at least one orifice or window 808 illustratively having a somewhat rectangular shape. The peripheral edges of the window 808 form a ledge 810 that is used in conjunction with a bur (FIG. 4) for performing the osteotomy, as discussed below in further detail. The size and shape of the window 808, as well as the depth or thickness of the ledge 810 are formed to correspond with the results of the CT scan and 3-D imaging software used for planning the osteotomy for a particular patient, such that the lower portion of the ledge 810 is aligned with and conforms to the shape of the bony floor of the sinus cavity and coronal portion of the maxilla.

Figure 4:
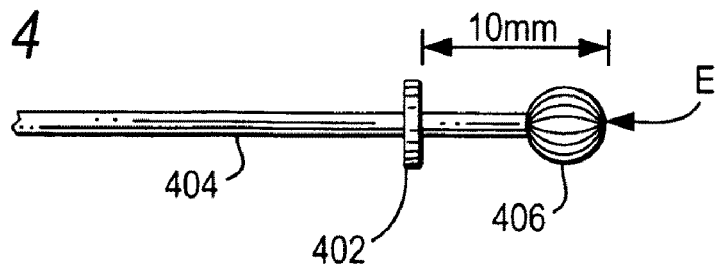
FIG. 4 shows a surgical bur having a depth guide in accordance with the present invention.

Referring now to FIG. 4, in another aspect of the present invention, a bur 400 with a depth guide 402 is then utilized to prepare the osteotomy within the outline of the window 808 inside the surgical guide 800. As shown in the drawing, the bur 400 includes an elongated shaft 404 having a cutting blade 406 affixed to an end of the shaft 404, as is well known in the art. The depth guide 402 is affixed transversely across the shaft at a distance of 10 mm from the endpoint (E) of the cutting blade 406, although such distance is not considered limiting.

For example, the surgical bur 400 can have an depth guide 402 which allows it to maintain a lesser depth, such as 5 mm from the edge of the guide 800 to the point of penetration of the sinus. This alternative size of the bur guide 402 can be used where the sinus wall is thin and 10 mm depth is not necessary in the depth guide 402.

Figure 5:
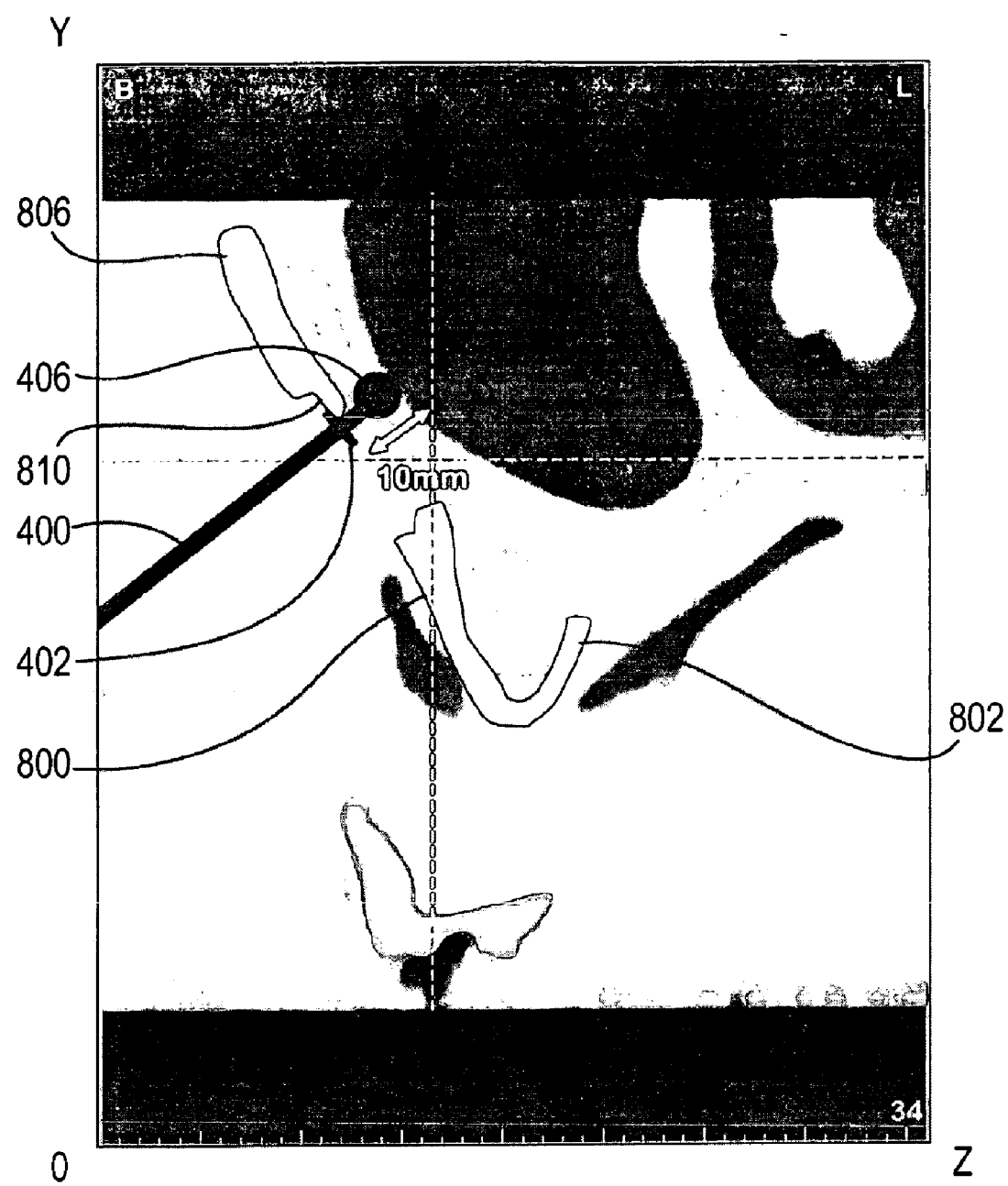
FIG. 5 shows the surgical guide of the present invention in position on the maxilla with the surgical bur, SB, in place resting on the ledge (L) of the surgical guide in order to penetrate the sinus along the apical portion of the osteotomy.

It is well known that the lateral wall of the maxillary bone adjacent to the maxillary sinus can typically have a thickness in the range of approximately 1-5 mm, although other variations in thicknesses are known to occur. Referring to FIGS. 4 and 5, as the thickness of the lateral wall of the maxillary bone varies, the thickness of the ledge 810 of the window 808 of the guide 800 will also vary along the ledge 810 depending on the thickness of the lateral wall of the maxillary bone to sum to a total of about 10 mm (guide thickness plus thickness of lateral wall of maxillary sinus), since the distance between the endpoint (E) of the distal end of the cutting blade 406 and the depth guide 402 of the bur 400 is at a constant 10 mm. For example, at locations of the maxilla that have a thickness of 2 mm, then the depth of the ledge 810 of the surgical guide 800 will be 8 mm (10 mm-2 mm). Similarly, where portions of the maxilla bone is, for example, 5.1 mm thick, then the ledge 810 will have a depth of 4.9 mm (10 mm-5.1 mm), and so forth. Accordingly, the thickness of the window ledge varies to conform to the unique shape and dimensions of the lateral wall of the patient's maxilla bone as it changes as each position along the X-Y or Y-X axes.

Figure 7:
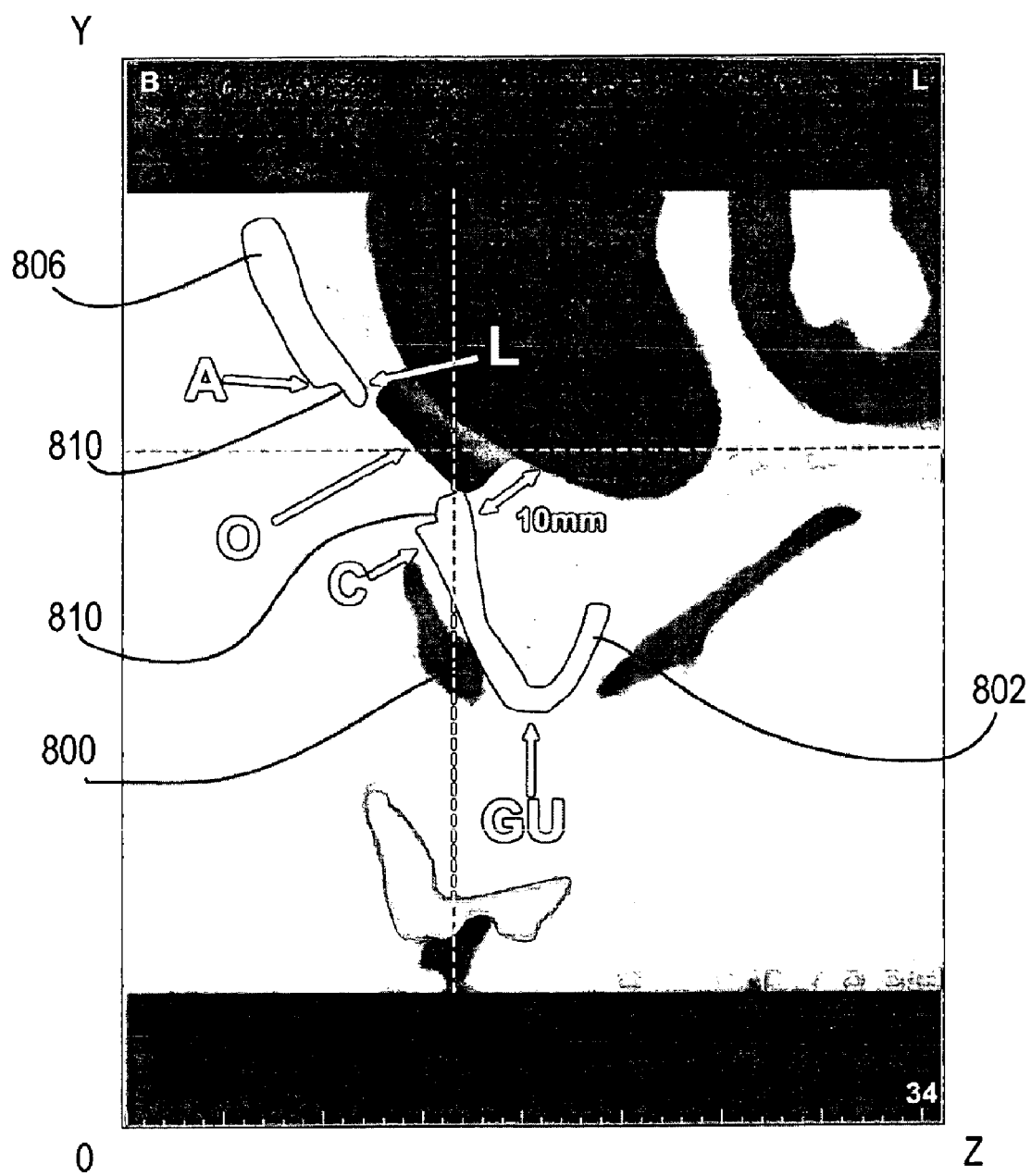
FIG. 7 is the same cross sectional view of FIGS. 3B and 5 showing the lateral wall of the sinus after the osteotomy (O) has been prepared.

Referring to FIG. 5, the bur 400 is positioned to rest on the ledge 810 within the window 808 of the guide 800 so as to maintain a constant cutting depth and not penetrate too far inside the sinus. The ledge 810 of the surgical guide 800 is illustratively shown as being thicker at the bottom (coronal portion) than at the top (apical portion) of the ledge 810. Referring to FIG. 7, after the osteotomy has been prepared, the bone within the window 808 of the osteotomy is elevated as the sinus is entered for elevation and grafting. Referring back to FIG. 3A, the portion of the maxilla receiving the bone graph (G) is illustratively shown.

Figure 9:
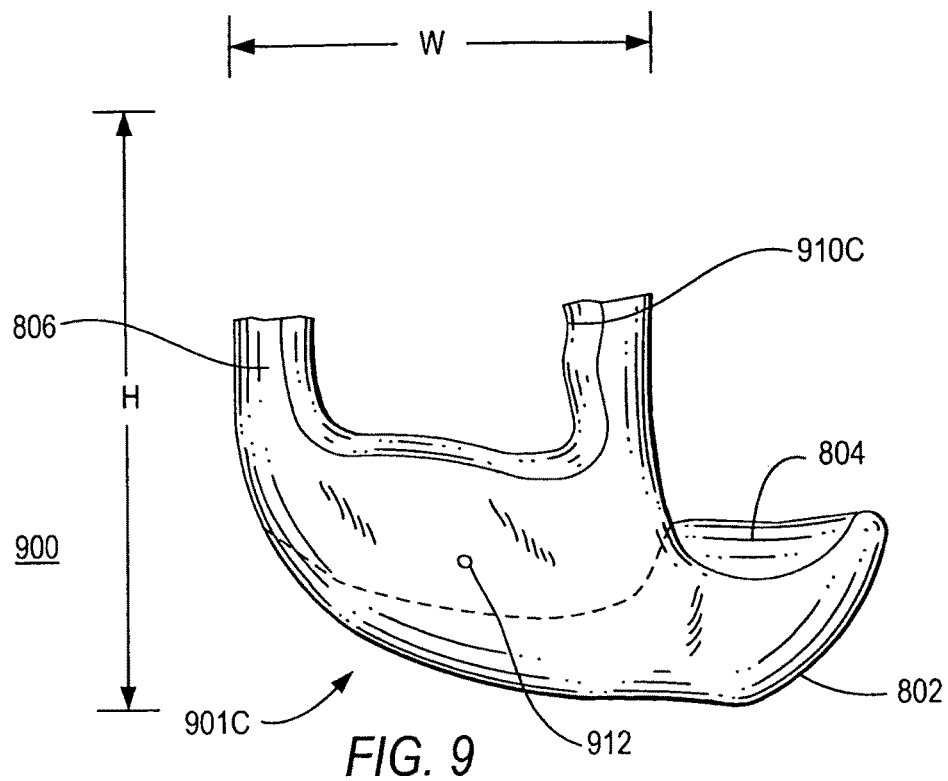
Figure 10:
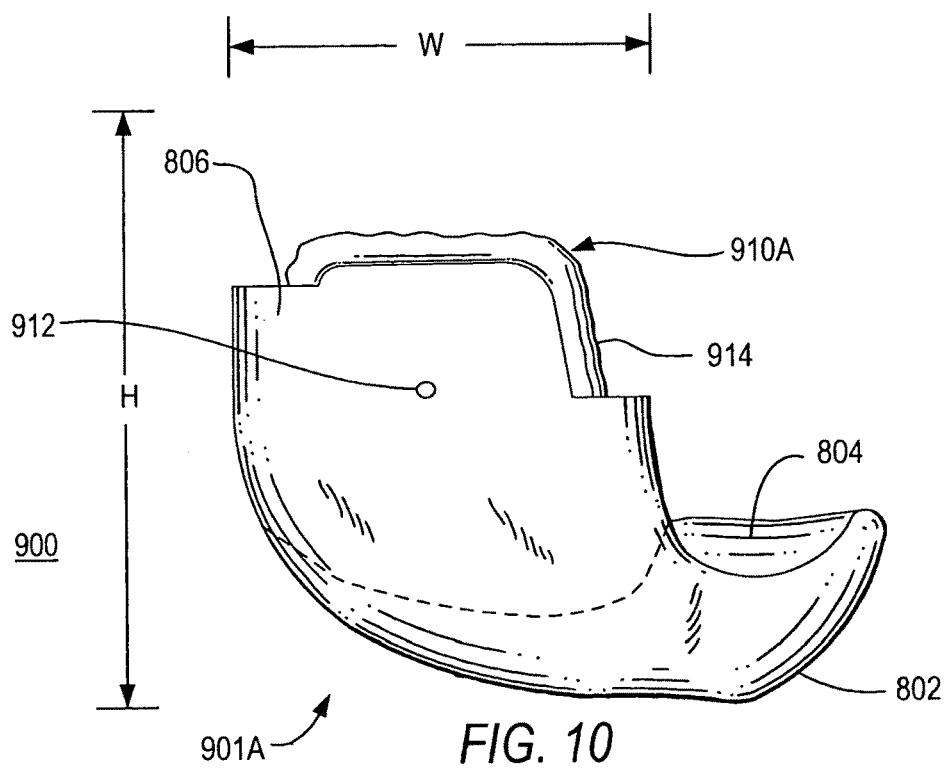

FIGS. 9 and 10 collectively depict an embodiment of a custom configured, multi-sectional surgical guide 900 suitable for performing the osteotomy. FIG. 9 illustrates a top, front perspective view of a first subsection 901C, and FIG. 10 illustrates a top, front perspective view of a second portion 901A of the multi-section surgical guide 900.

Referring to FIG. 9, the first subsection 901C of the surgical guide 900 includes a first ledge 910C for forming the coronal (arrow C in FIG. 3B) border of the osteotomy. The shape and configuration of the first ledge 910C is custom configured based on the treatment plan of the patient in a similar manner as described above with respect to the surgical guide 800 of FIG. 8. That is, The size and shape of the first subsection 901C, including length, height and the depth or thickness of the ledge 910C are formed to correspond with the results of the CT scan and 3-D imaging software used for planning the osteotomy for a particular patient. In the illustrative embodiment, the first ledge 910C is somewhat semi-lunar or crescent shaped, although these shapes are not considered limiting. For example, the first ledge 910 can be U-shaped, among other shapes.

Referring to FIG. 10, the second subsection 901A of the surgical guide 900 similarly includes a second ledge 910A for forming the apical (arrow A in FIG. 3B) border of the osteotomy. The shape and configuration of the second ledge 910A is custom configured based on the treatment plan of the patient in a similar manner as described above with respect to the surgical guide 800 of FIG. 8. That is, The size and shape of the second subsection 901A, including length, height and the depth or thickness of the second ledge 910A are formed to correspond with the results of the CT scan and 3-D imaging software used for planning the osteotomy for a particular patient. In the illustrative embodiment, the second ledge 910A is also somewhat semi-lunar or crescent shaped, although these shapes are not considered limiting. For example, the first ledge 910 can be U-shaped, among other shapes. Therefore, in a similar manner as the surgical guide 800 of FIG. 8, the surgical guide 900 is uniquely shaped to correspond to the particular, unique and irregular shape of the maxillary bone and adjacent structures of the patient.

In operation, the surgeon attaches one of the subsections, e.g., subsection 901C, over the maxillary bone, for example, by inserting a fastener through orifice 912 and into the maxillary bone to secure the first subsection 901C thereon. The surgeon then uses the bur 400 to cut along the length of the customized first ledge 910C to expose the coronal portion of the maxilla. The surgeon cuts directly along the ledge in a similar manner as described above with respect to the bur 400 and surgical guide 800 of FIGS. 4 and 8. Thereafter, the first subsection 901C is removed, and the surgeon attaches the second subsection 901A over the maxillary bone by inserting the fastener through orifice 912 and into the maxillary bone to secure the second subsection 901A thereon. The surgeon then uses the bur 400 again to cut along the length of the customized second ledge 910A to expose the bony floor of the sinus cavity.

Once the second subsection 901A is removed from the patient, the two sequential cutting procedures form a window along the lateral wall to perform a bone graph, as required. The window along the lateral wall is configured based on the two ledge portions 910C and 910A of the pair of surgical guide subsections 901C and 901A. Accordingly, instead of using the single piece guide 800 of FIG. 8, the same window 808 (i.e., exposed area on the patient) can be formed by using a multi-sectional guide 900 as illustratively shown with respect to FIGS. 9 and 10.

A multi-sectional guide 900 is useful in instances where the shape and dimensions along the lateral wall of the maxillary bone in the patients mouth are difficult to attach a single surgical guide. For example, a single surgical guide having both the superior and inferior ledges, such as the guide 800, may impinge on structures adjacent the superior ledge, such as the zigomatic process (cheek bone) or the infraorbital nerve, and the like. Thus, the multi-sectional guide 900 of the present invention enables the surgeon to sequentially attach smaller guides in the patients mouth to sequentially make the necessary cuts along the ledges 910C and 910A, such that when all of the cuts have been made, a single window is formed along the lateral wall of the patient.

Figure 11:
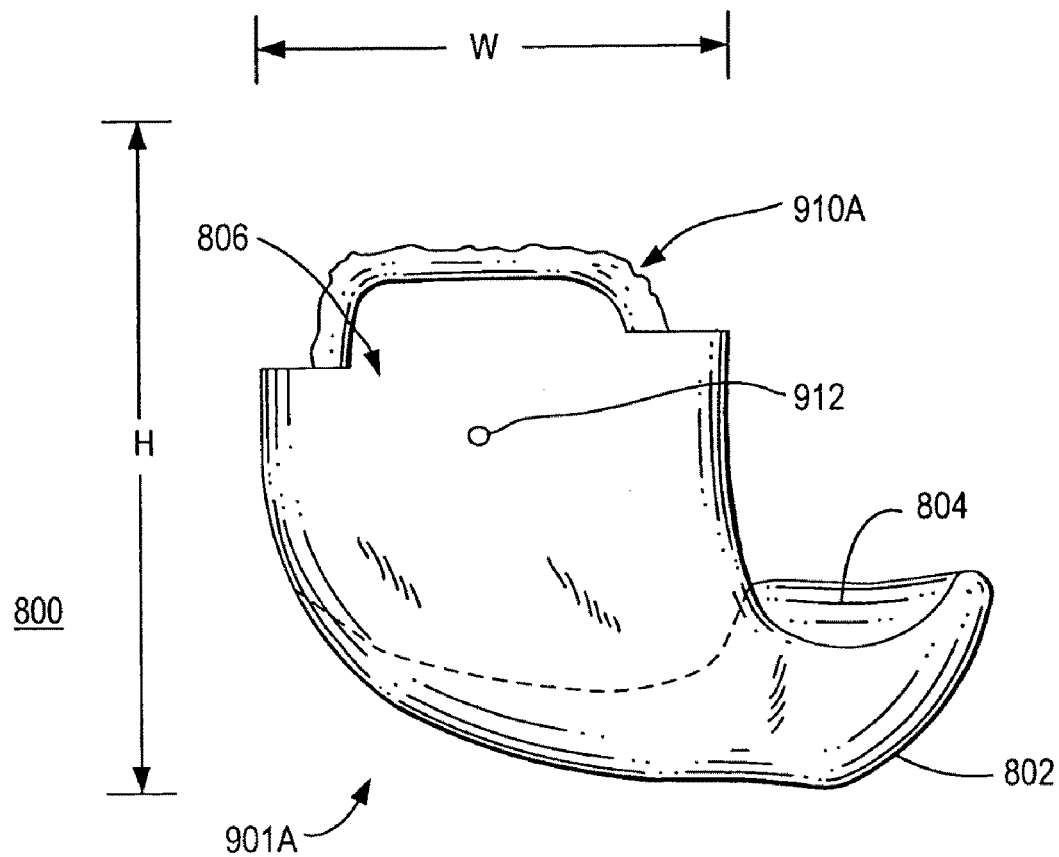
FIG. 11 is a top perspective view of a second portion of the multi-section surgical guide illustrating an alternative configuration.

Referring to FIG. 11, a second subsection 901A of the surgical guide 900 is illustratively shown. This second subsection 901A includes a differently shaped ledge 910A than the ledge shown in FIG. 10 to illustrate that the configurations of the surgical guides are unique to each patient based on the results of the CT scan and 3-D imaging software used for planning the osteotomy for a particular patient. The second subsection 901A of FIG. 11 will be matched with a corresponding first subsection (not shown) in a similar manner as provided above with respect to the surgical guide subsections of FIGS. 9 and 10.

As noted above, the guide can be of several pieces or sections, each one having a generally semi-lunar shaped ledge, which corresponds to a particular portion of the osteotomy, whether it is the apical, coronal, mesial or distal portion, that when all the subsections of the guide are sequentially seated and the osteotomies corresponding to such subsections are made, the entire osteotomy is created to allow the window to be opened. The size and shape of the semi-lunar ledges, as well as the depth or thickness of the ledges are formed to correspond with the results of the CT scan and 3-D imaging software used for planning the osteotomy for a particular patient, such that the edge of the ledges are aligned with and conforms to the shape of the bony floor of the sinus cavity and coronal portion of the maxilla. Moreover, the ledges of the paired subsections can be formed to include some overlap. For example, when the first subsection is attached and the cuts are made, once the first subsection is removed and the second subsection is attached, the opposing distal ends (e.g., distal end 914 in FIG. 10) of the ledges will be adjacent to a portion of the cuts made while using the first subsection guide.

Although an exemplary description of the invention has been set forth above to enable those of ordinary skill in the art to make and use the invention, that description should not be construed to limit the invention, and various modifications and variations may be made to the description without departing from the scope of the invention, as will be understood by those with ordinary skill in the art, and the scope thereof is determined by the claims that follow.

I claim:

1. Surgical guide for performing a sinus elevation procedure on a specific patient's maxillary sinus by penetrating a lateral bony wall proximate a maxillary sinus of the patient with a bur, said lateral wall having an external surface, and a varying length, height and depth extending along an X-axis, a Y-axis, and a Z-axis, respectively, said surgical guide comprising:

a first curvilinear-shaped subsection for placement adjacent to and in direct and continuous contact with the external surface of said lateral wall of the maxillary sinus, said first curvilinear-shaped subsection having at least one elongated first ledge having a length that extends in a direction along the X-axis of the lateral wall, the first ledge having varying surface contours formed in X-Y and Z-X planes extending along the length to correspond to and align with surface contours formed in X-Y and Z-X planes of the lateral wall at the surgical site, the first ledge being configured to provide continuous contact with the lateral wall along its entire length at a first area of the surgical site; and a second curvilinear-shaped subsection for sequential placement adjacent to and in direct and continuous contact with the external surface of said lateral wall of the maxillary sinus, said second curvilinear-shaped subsection having at least one elongated second ledge having a length that extends in a direction along the X-axis of the lateral wall, the second ledge having varying surface contours formed in X-Y and Z-X planes extending along the length to correspond to and align with surface contours formed in the X-Y and Z-X planes of the lateral wall at the surgical site, the second ledge being configured to provide continuous contact with the lateral wall along its entire length at a second area of the surgical site;

wherein the first and second ledges each include variable depths in the Z-X plane and are configured to directly correspond to thickness variations along the Z-X plane of the patient's lateral wall, said first and second ledges permitting movement, guidance and depth control of the bur in three-dimensions.

2. The surgical guide of claim 1, wherein said first curvilinear-shaped subsection includes: a first lower portion having a custom-fabricated surface configured for positioning in intimate contact with and over an alveolar ridge of the maxillary bone and/or adjacent teeth of said patient; and a second upper portion extending upward from said lower portion for positioning adjacent to and in direct contact with said lateral wall of the maxillary sinus to define the first area of the surgical site.

3. The surgical guide of claim 2, wherein said second curvilinear-shaped subsection includes: a second lower portion having a custom-fabricated surface configured for positioning in intimate contact with and over an alveolar ridge of the maxillary bone and/or adjacent teeth of said patient; and a second upper portion extending upward from said lower portion for positioning adjacent to and in direct contact with said lateral wall of the maxillary sinus to define the second area of the surgical site.

4. The surgical guide of claim 3, wherein the first lower portion of the first curvilinear-shaped subsection is configured the same as the second lower portion of the second curvilinear-shaped subsection.

5. The surgical guide of claim 4, wherein the second upper portion of the second curvilinear-shaped subsection extends upward a height from the second lower portion of the second curvilinear-shaped subsection greater than the first upper portion of the first curvilinear-shaped subsections extends from its respective lower portion.

6. The surgical guide of claim 1, wherein said at least one elongated first ledge includes at least one of a lower inferior ledge portion having a surface shaped to correspond in shape to an inferior portion of the patient's sinus, an anterior ledge portion having a surface shaped to correspond to an anterior portion of the patient's sinus, or a posterior ledge portion having a surface shaped to correspond to a posterior portion of the patient's sinus, each of said inferior, anterior, or posterior ledge portions defining a customized outline guide which corresponds specifically to the first area of the surgical site for penetrating the lateral wall of the patient's maxillary sinus.

7. The surgical guide of claim 1, wherein said at least one elongated first ledge includes at least one of an anterior ledge portion having a surface shaped to correspond to an anterior portion of the patient's sinus, a posterior ledge portion having a surface shaped to correspond to a posterior portion of the patient's sinus, or an upper superior ledge portion having a surface shaped to correspond to a superior portion of the patient's sinus, each of said anterior, posterior and superior ledge portions defining a customized outline guide which corresponds specifically to the second area of the surgical site for penetrating the lateral wall of the patient's maxillary sinus.

8. A surgical guide system for performing a sinus elevation procedure by penetrating an outer surface of an irregularly-shaped lateral wall of a maxillary bone forming a maxillary sinus of a specific patient, the system comprising:
   a treatment plan including a CT-scan and three-dimensional images which characterize a plurality of walls defining the maxillary sinus and maxillary bone structures of the patient, said plurality of walls having irregular dimensions, shapes, and contours formed along surface portions of the walls that are unique to each patient, said lateral wall having a length extending along an X-axis, a height extending along a Y-axis, and a depth extending along a Z-axis, said lateral wall having a convex-shape extending along the X-axis;
   a dental bur;
   a first curvilinear-shaped subsection for placement adjacent to and in direct and continuous contact with an external surface of said lateral wall of the maxillary sinus, said first curvilinear-shaped section having at least one elongated first ledge having a length that extends in a direction along the X-axis of the lateral wall, the first ledge having varying surface contours formed in X-Y and Z-X planes extending along the length to correspond to and align with surface contours formed in X-Y and Z-X planes of the lateral wall to define a surgical site, the first ledge being configured to provide continuous contact with the lateral wall along its entire length and to guide the dental bur at a first area of the surgical site; said first elongated ledge having a customized variable depth along the Z-axis which corresponds to and aligns with thickness variations of the patient's lateral wall, said first elongated ledge permitting movement, guidance and depth control of a dental bur in three-dimensions along the first area of the surgical site;
   a second curvilinear-shaped subsection for placement adjacent to and in direct and continuous contact with the external surface of said lateral wall of the maxillary sinus, said second curvilinear-shaped section having at least one elongated second ledge having a length that extends in a direction along the X-axis of the lateral wall, the second ledge having varying surface contours formed in X-Y and Z-X planes extending along the length to correspond to and align with surface contours formed in the X-Y and Z-X planes of the lateral wall at the surgical site, the second ledge being configured to provide continuous contact with the lateral wall along its entire length and to guide the dental bur at a second area of the surgical site; said second elongated ledge having a customized variable depth along the Z-axis which corresponds to and aligns with thickness variations of the patient's lateral wall, said second elongated ledge permitting movement, guidance and depth control of a dental bur in three-dimensions along the second area of the surgical site; and
   wherein the first and second curvilinear-shaped subsections are customized in shape and dimension to conform to the unique and irregularly-shaped and dimensioned lateral wall of the patient's maxillary bone at the surgical site, as determined by the CT-scan and three-dimensional images of the treatment plan.

9. The surgical guide system of claim 8, wherein said treatment plan comprises at least one of a panoramic, coronal, sagittal and three-dimensional view of the maxillary sinus and maxillary bone structures of said patient.

10. The surgical guide system of claim 8, wherein the bur is configured to trace and cut the lateral wall at the surgical site while in contact and moving along at least one of the first and second ledge.

11. The surgical guide of claim 10, wherein said bur comprises: an elongated shaft having opposing first and second ends, said first end configured for insertion into a rotary device; a cutting blade coupled to the second end of said shaft; and a depth guide extending transversely from said shaft and spaced a predetermined distance from a distal end of said cutting blade.

12. The surgical guide of claim 11, wherein said depth guide traverses said shaft a distance in a range of approximately 5-10 mm from the distal end of the cutting blade.

13. The surgical guide of claim 8, wherein said depth guide is configured to interface with and traverse along said first and second ledges of said corresponding first and second curvilinear-shaped subsections.

14. A method of performing sinus elevation surgery to penetrate a bony lateral wall proximate a maxillary sinus of a specific patient, comprising:
   providing a treatment plan including a CT-scan and three-dimensional images which characterize a plurality of walls defining the maxillary sinus and maxillary bone structures of the patient, said plurality of walls having irregular dimensions, shapes, and contours formed along surface portions of the walls that are unique to each patient, said lateral wall having a length extending along an X-axis, a height extending along a Y-axis, and a depth extending along a Z-axis, said lateral wall having a convex-shape extending along the X-axis;
   providing a first curvilinear-shaped subsection for placement adjacent to and in direct and continuous contact with an external surface of said lateral wall of the maxillary sinus, said first curvilinear-shaped subsection having at least one elongated first ledge having a length that extends in a direction along the X-axis of the lateral wall, the first ledge having varying surface contours formed in X-Y and Z-X planes extending along the length to correspond to and align with surface contours formed in X-Y and Z-X planes of the lateral wall to define a surgical site, the first ledge being configured to provide continuous contact with the lateral wall along its entire length and to guide a dental bur at a first area of the surgical site; said first elongated ledge having a customized variable depth along the Z-axis which corresponds to and aligns with thickness variations of the patient's lateral wall, said first elongated ledge permitting movement, guidance and depth control of the dental bur in three-dimensions along the first area of the surgical site;

providing a second curvilinear-shaped subsection for placement adjacent to and in direct and continuous contact with the external surface of said lateral wall of the maxillary sinus, said second curvilinear-shaped subsection having at least one elongated second ledge having a length that extends in a direction along the X-axis of the lateral wall, the second ledge having varying surface contours formed in X-Y and Z-X planes extending along the length to correspond to and align with surface contours formed in the X-Y and Z-X planes of the lateral wall at the surgical site, the second ledge being configured to provide continuous contact with the lateral wall along its entire length and to guide the dental bur at a second area of the surgical site; said second elongated ledge having a customized variable depth along the Z-axis which corresponds to and aligns with thickness variations of the patient's lateral wall, said second elongated ledge permitting movement, guidance and depth control of the dental bur in three-dimensions along the second area of the surgical site; and wherein the first and second curvilinear-shaped subsections are customized in shape and dimension to conform to the unique and irregularly-shaped and dimensioned lateral wall of the patient's maxillary bone at the surgical site, as determined by the CT-scan and three-dimensional images of the treatment plan.

15. The method of claim 14, further comprising: fixedly placing said first curvilinear-shaped subsection over a portion of an alveolar ridge and/or adjacent teeth, and a first portion of a lateral wall of the maxillary sinus of said patient after reflection of a corresponding overlying buccal mucosa; cutting a first portion of said maxillary bone at the first area of the surgical site as defined by the customized first ledge by guiding the bur along the customized first ledge; and removing said first curvilinear-shaped subsection from placement over the lateral wall once the cutting is complete.

16. The method of claim 15, further comprising: fixedly placing said second curvilinear-shaped subsection over a portion of an alveolar ridge and/or adjacent teeth, and a second portion of a lateral wall of the maxillary sinus of said patient after reflection of a corresponding overlying buccal mucosa; cutting a second portion of said maxillary bone at the second area of the surgical site as defined by the customized second ledge by guiding the bur along the customized second ledge; and removing said second curvilinear-shaped subsection from placement over the lateral wall once the cutting is complete.

17. The method of claim 16, further comprising providing a bone graft in a portion of the maxillary bone and sinus as defined in the treatment plan.

18. The method of claim 16, wherein each of the cutting steps comprises providing the bur with a depth guide set a predetermined distance from a distal end of a cutting blade of the bur based on thickness of the maxillary bone structures of said patient acquired during said treatment plan.

19. The method of claim 15, wherein said placing the first curvilinear-shaped subsection step further comprises securing said first curvilinear-shaped subsection over the alveolar ridge and/or adjacent teeth and lateral wall of the maxillary sinus, such that the first ledge is aligned at a floor portion of the sinus with a positive seat regardless of variations in height of said floor portion.

20. The method of claim 16, wherein said placing the second curvilinear-shaped subsection step further comprises securing said second curvilinear-shaped subsection over the alveolar ridge and/or adjacent teeth and lateral wall of the maxillary sinus, such that the second ledge is aligned at a superior portion of the sinus with a positive seat regardless of variations in height of said superior portion.

* * * * *